United States Patent
Wang et al.

(10) Patent No.: US 10,654,770 B2
(45) Date of Patent: May 19, 2020

(54) PRODUCTION OF NEOPENTANE

(71) Applicant: ExxonMobil Chemical Patents Inc., Baytown, TX (US)

(72) Inventors: Kun Wang, Bridgewater, NJ (US); Lorenzo C. DeCaul, Langhorne, PA (US); James R. Lattner, La Porte, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/324,634

(22) PCT Filed: Aug. 18, 2017

(86) PCT No.: PCT/US2017/047580
§ 371 (c)(1),
(2) Date: Feb. 11, 2019

(87) PCT Pub. No.: WO2018/044591
PCT Pub. Date: Mar. 8, 2018

(65) Prior Publication Data
US 2019/0177248 A1  Jun. 13, 2019

Related U.S. Application Data

(60) Provisional application No. 62/380,515, filed on Aug. 29, 2016.

(51) Int. Cl.
*C07C 4/08* (2006.01)
*C07C 2/06* (2006.01)
(Continued)

(52) U.S. Cl.
CPC .................. *C07C 4/10* (2013.01); *C07C 2/10* (2013.01); *C07C 2/12* (2013.01); *C07C 2521/06* (2013.01);
(Continued)

(58) Field of Classification Search
CPC ..................................... C07C 2/06; C07C 4/08
(Continued)

(56) References Cited

U.S. PATENT DOCUMENTS 2,325,052 A  7/1943  Grosse et al.
2,394,743 A  2/1946  Bergsteinsson
(Continued)

FOREIGN PATENT DOCUMENTS

GB  574694  1/1946
GB  1220015  4/1967
(Continued)

OTHER PUBLICATIONS

Graves, "STRATCO Effluent Refrigerated H2SO4 Alkylation Process," in Handbook of Petroleum Refining Processes, Third Edition, ch. 1.2 (2004).
(Continued)

*Primary Examiner* — Thuan D Dang
(74) *Attorney, Agent, or Firm* — Kevin M. Faulkner

(57) ABSTRACT

Disclosed herein are processes for producing neopentane. The processes generally relate to demethylating diisobutylene to produce neopentane. The diisobutylene may be provided by the dimerization of isobutylene.

16 Claims, 1 Drawing Sheet

(51) Int. Cl.
*C07C 4/10* (2006.01)
*C07C 2/10* (2006.01)
*C07C 2/12* (2006.01)

(52) U.S. Cl.
CPC .... *C07C 2521/16* (2013.01); *C07C 2523/755* (2013.01); *C07C 2529/40* (2013.01)

(58) Field of Classification Search
USPC ...................................... 585/310, 510, 752
See application file for complete search history.

(56) References Cited

U.S. PATENT DOCUMENTS

| | | | |
|---|---|---|---|
| 2,413,691 | A | 1/1947 | Crawford et al. |
| 2,422,670 | A | 6/1947 | Haensel et al. |
| 2,422,672 | A | 6/1947 | Haensel et al. |
| 2,422,674 | A | 6/1947 | Haensel et al. |
| 2,422,675 | A | 6/1947 | Haensel et al. |
| 2,436,923 | A | 3/1948 | Haensel et al. |
| 3,585,252 | A | 6/1971 | Kennedy |
| 3,660,516 | A | 5/1972 | Crain et al. |
| 3,755,493 | A | 8/1973 | Norel |
| 3,855,346 | A | 12/1974 | Norel |
| 4,593,147 | A | 6/1986 | Butter et al. |
| 4,940,829 | A | 7/1990 | Drake |
| 5,146,037 | A | 9/1992 | Zarchy et al. |
| 6,262,192 | B1 | 7/2001 | Wu |
| 2007/0043247 | A1 | 2/2007 | Webber et al. |
| 2010/0145122 | A1* | 6/2010 | Zak .................. C07C 1/24 585/506 |

FOREIGN PATENT DOCUMENTS

| | | |
|---|---|---|
| WO | 2018/044591 | 3/2018 |
| WO | 2018/044592 | 3/2018 |
| WO | 2018/044596 | 3/2018 |

OTHER PUBLICATIONS

Roeseler, "UOP AlkyleneTM Process for Motor Fuel," in Handbook of Petroleum Refining Processes, Third Edition, ch. 1.3 (2004).
Himes et al., "UOP HF Alkylation Technology," in Handbook of Petroleum Refining Processes, Third Edition, ch. 1.2 (2004).
Cusher, "UOP Penex Process," Handbook of Petroleum Refining Processes, Third Edition, Ch. 9.3 (2004).
Matsumoto et al., "Contrast between nickel and platinum catalysts in hydrogenolysis of saturated hydrocarbons," Journal of Catalysis, vol. 19(2), p. 101 (1970).
Matsumoto et al., "The classification of metal catalysts in hydrogenolysis of hexane isomers," Journal of Catalysis, vol. 22, pp. 182-192 (1971).
Paál et al, "On the pattern of hydrogenolysis of hexane isomers over four Group VIIIB metals," Reaction Kinetics and Catalysis Letters, vol. 12(2), pp. 131-37 (1979).
Richardson J. et al , "Preparation variables in nickel catalysts", J. Catal. 54, 207-218, 1978.
Schepers F.J., "Apparent particle size sensitivity in hydrocarbon reactions," J. Catal. 96, 82-87, 1985.
Richardson J. et al., "Crystallite Size Distributions and Stabilities of Homogeneously Deposited Ni/SiO2 Catalysts," Stu. Surf. Sci. Catal. 3, 131-142, 1979.
Coenen J., "Catalytic hydrogenation of fatty oils," Ind. Eng. Chem. Fundamen. 25 (1) 43-52, 1986.
Song C. et al., "Properties of the Ni/Kieselguhr catalysts prepared by precipitation method," Korean J. of Chem. Eng. 9 (3) 159-163, 1992.
Mendioroz S. et al., "Effect of the method of preparation on the activity of nickel Kieselguhr catalyst for vegetable oil hydrogenation," Appl. Catal. 66, 73-90, 1990.
Hadley, G.R., "Thermal conductivity of packed metal powders," International Journal of Heat and Mass Transfer 29.6, 909-920, 1986.
Avdonina, E.N., "Reactions of tritium recoil atoms in liquid mixtures of isooctane with benzene," XP002768312 & vol. 15, No. 5, 1973, pp. 720-726.
Zidek, Zdeno et al., "Nickel-silica-alumina catalysts. III. Catalytic properties. Hydrocracking of isooctane", 1969.
Seth et al., "Selective hydrogenation of 1,3-butadiene in mixture with isobutene on a Pd/@a-alumina catalyst in a semi-batch reactor", vol. 62, No. 17, 2007.
Clarke et al., "The Preparation and Activity for Alkane Reactions of Aerosil-Supported Rhodium-Copper Clusters," Journal of Catalysis, vol. 111, pp. 374-382 (1988).
Haensel et al., "Selective Demethylation of Paraffin Hydrocarbons: Preparation of Triptane and Neopentane," Industrial and Engineering Chemistry, vol. 39, pp. 853-857 (1947).
Foger et al., "Skeletal Reactions of Hydrocarbons over Supported Iridium-Gold Catalysts," Journal of Catalysis, vol. 64, pp. 448-463 (1980).
Vogelzang et al., "Reactions of 2,2-Dimethylbutane on Iridium: The Role of Surface Carbonaceous Layers and Metal Particle Size," Journal of Catalysis, vol. 111, pp. 77-87 (1988).
Machiels, et al., "Hydrogenolysis of 2,2-Dimethylbutane and n-Hexane over Supported Ruthenium, Nickel, Cobalt, and Iron," Journal of Catalysis, vol. 58, pp. 268-275 (1979).
Leclercq et al., "Hydrogenolysis of Saturated Hydrocarbons: Influence of Hydrocarbon Structures on the Activity and Selectivity of Nickel on Silica," Journal of Catalysis, vol. 99, pp. 1-11.
Birkhoff et al., "NExOCTANETM Technology for Isooctane Production," in Handbook of Petroleum Refining Processes, Third Edition, Ch. 1.1 (2004).
Kranz, K., "Alkylation chemistry-Mechanism, operating variables, and olefin interactions", DuPont Company, 2003.
Zimmer, H. et al., "Hydrogenolysis of alkanes with quaternary carbon atoms over Pt and Ni black catalysts", J.Chem. Soc., Fararday Trans. 1, 1982.

* cited by examiner

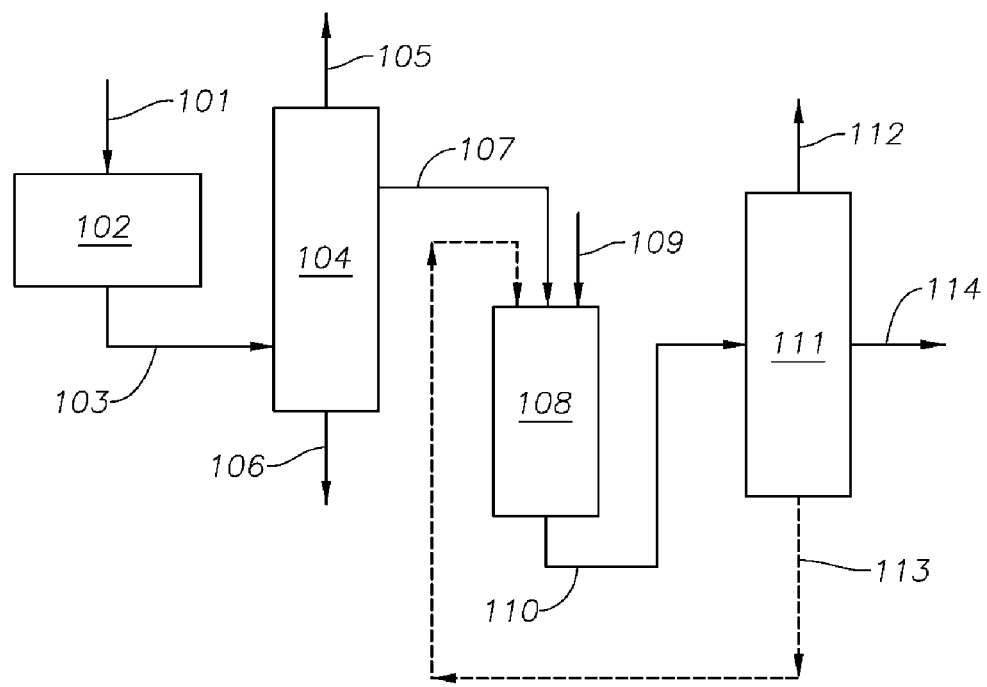

PRODUCTION OF NEOPENTANE

CROSS REFERENCES TO RELATED APPLICATIONS

This invention is a National Phase Application claiming priority to PCT Application Serial No. PCT/US2017/047580 filed Aug. 18, 2017, which claims priority to and benefit of U.S. Ser. No. 62/380,515, filed Aug. 29, 2016 and EP 16194992.0, filed Oct. 21, 2016, the disclosures of which are incorporated by reference.

FIELD OF THE INVENTION

The present invention relates to methods of producing neopentane and uses thereof.

BACKGROUND OF THE INVENTION

Neopentane is a unique nonpolar hydrocarbon molecule that has found industrial use in the form of an inert condensing agent for gas-phase reactions. See, for instance, U.S. Pat. No. 6,262,192. Other potential industrial uses for neopentane include use as a heat removal agent, a blowing agent, and a gasoline blend component due to its relatively high octane numbers. For instance, neopentane has a Research Octane Number (RON) of 85.5 and a Motor Octane Number (MON) of 80.2.

Currently, there is no satisfactory process for producing neopentane on a commercial scale. For example, typical existing processes for synthesizing neopentane utilize stoichiometric reactions of t-butylchloride and a Grignard reagent, methyl aluminum dichloride, dimethyl aluminum chloride, or trimethyl aluminum. See, for instance, U.S. Pat. No. 3,585,252. Such stoichiometric reactions generate large amounts of metal halides and are difficult to scale up to produce neopentane at commercial quantities. Likewise, though neopentane may be synthesized by hydrogenation of neopentanoic acid under high pressure and at high temperature, e.g., as described in U.S. Pat. No. 4,593,147, such processes are expensive due to the neopentanoic acid feedstock and suffer from a combination of demanding reaction conditions and low selectivity.

Other proposed processes for producing neopentane involve demethylation of higher carbon number branched paraffins. For example, U.S. Pat. Nos. 4,940,829 and 2,422,675 each relate to the preparation of neopentane via catalytic demethylation of neohexane. However, these higher carbon number branched paraffins are not readily available in high concentrations suitable as feedstock that could be utilized on a commercial scale.

Yet alternatively, a process for producing neopentane by hydrogenating an isobutylene polymer and selectively cracking the hydrogenation product is described in U.S. Pat. No. 2,394,743. However, in addition to producing neopentane, this process also produces large amounts of heavier hydrocarbon components.

Thus, there remains a need for processes for producing neopentane at high yield under mild reaction conditions and utilizing low cost, readily available feedstock. Such processes would allow economic production of neopentane at commercial quantities.

Other references of interest include: "The Preparation and Activity for Alkane Reactions of Aerosil-Supported Rhodium-Copper Clusters," Clarke et al., *Journal of Catalysis*, vol. 111, pp. 374-82 (1988); "Selective Demethylation of Paraffin Hydrocarbons: Preparation of Triptane and Neopentane," Haensel et al., *Industrial and Engineering Chemistry*, vol. 39, pp. 853-57 (1947); "Skeletal Reactions of Hydrocarbons over Supported Iridium-Gold Catalysts," Foger et al., *Journal of Catalysis*, vol. 64, pp. 448-63 (1980); "Reactions of 2,2-Dimethylbutane on Iridium: The Role of Surface Carbonaceous Layers and Metal Particle Size," Vogelzang et al., *Journal of Catalysis*, vol. 111, pp. 77-87 (1988); "Hydrogenolysis of 2,2-Dimethylbutane and n-Hexane over Supported Ruthenium, Nickel, Cobalt, and Iron," Machiels, et al., *Journal of Catalysis*, vol. 58, pp. 268-75 (1979); "Hydrogenolysis of Saturated Hydrocarbons: Influence of Hydrocarbon Structures on the Activity and Selectivity of Nickel on Silica," Leclercq et al., *Journal of Catalysis*, vol. 99, pp. 1-11; G.B. Patent Publication No. 574694; U.S. Pat. Nos. 2,422,670; 2,436,923; and "NExOCTANE™ Technology for Isooctane Production," in Handbook of Petroleum Refining Processes, Third Edition, Birkhoff et al., Ch. 1.1 (2004).

SUMMARY OF THE INVENTION

The present invention relates to novel processes that address the need for the production of neopentane at high yield, under mild reaction conditions, and utilizing readily available feedstock. In one aspect, the present invention relates to a process for producing neopentane comprising dimerizing isobutylene to produce diisobutylene, followed by demethylating the diisobutylene to produce a product comprising at least 10 wt % neopentane. Typically, the isobutylene can be provided in a $C_4$ olefinic feed stream, preferably a refinery raffinate stream, such as a raffinate stream obtained from cracking naphtha. In another aspect the present invention relates to a process for producing neopentane comprising demethylating diisobutylene to produce a product comprising at least 10 wt % neopentane.

BRIEF DESCRIPTION OF THE DRAWINGS

The FIGURE is a diagram of a process of making neopentane.

DETAILED DESCRIPTION OF THE EMBODIMENTS

Described herein are processes for producing neopentane. As discussed below, the processes involve the demethylation of diisobutylene, preferably via contacting the diisobutylene with hydrogen in the presence of a catalyst. The diisobutylene can be provided by dimerization, preferably catalytic dimerization, of isobutylene. Preferably, the isobutylene is provided in a $C_4$ olefinic feed, such as a refinery raffinate stream. Alternatively, the diisobutylene can be provided in an independent feed stream. Preferably, the processes described herein enable the production of neopentane in quantities of greater than about 5 kg/hr, preferably greater than about 500 kg/hr, preferably greater than about 5000 kg/hr, and preferably greater than about 35000 kg/hr.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a fractionation column" include embodiments where one, two or more fractionation columns are used, unless specified to the contrary or the context clearly indicates that only one fractionation column is used. Likewise, "a $C_{12}+$ component" should be interpreted to include one, two or more $C_{12}+$ components unless specified or indicated by the context to mean only one specific $C_{12}+$ component.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, the concentrations of the various components of the first feedstock are expressed based on the total weight of the first feedstock. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, $6^{th}$ Edition, by F. Albert Cotton et al. (John Wiley & Sons, Inc., 1999).

As used herein, "hydrocarbon" refers to molecules or segments of molecules containing primarily hydrogen and carbon atoms. As used herein, the term "$C_n$" hydrocarbon wherein n is a positive integer, e.g., 1, 2, 3, 4, etc., means a hydrocarbon having n number of carbon atom(s) per molecule. The term "$C_n+$" hydrocarbon wherein n is a positive integer, e.g., 1, 2, 3, 4, etc., as used herein, means a hydrocarbon having at least n number of carbon atom(s) per molecule. The term "$C_n-$" hydrocarbon wherein n is a positive integer, e.g., 1, 2, 3, 4, etc., used herein, means a hydrocarbon having no more than n number of carbon atom(s) per molecule.

As used herein, "olefin" refers to any unsaturated hydrocarbon having the formula $C_nH_{2n}$, and containing one carbon-carbon double bond, wherein C is a carbon atom, H is a hydrogen atom, and n is the number of carbon atoms in the olefin.

As used herein, "alkane" or "paraffin" refers to any saturated hydrocarbon having the formula $C_nH_{2n+2}$, wherein C is a carbon atom, H is a hydrogen atom, and n is the number of carbon atoms in the alkane.

As used herein, a "primary carbon atom" refers to a carbon atom neighboring one carbon atom, "secondary carbon atom" refers to a carbon atom neighboring two carbon atoms, "tertiary carbon atom" refers to a carbon atom neighboring three carbon atoms, and "quaternary carbon atom" refers to a carbon atom neighboring four carbon atoms.

As used herein, the prefix "normal" or "n-" signifies a linear unbranched hydrocarbon.

As used herein, the prefix "iso" or "i-" signifies a hydrocarbon containing a methyl substitution at the second carbon of the hydrocarbon chain.

As used herein, the prefix "neo" signifies a hydrocarbon containing a quaternary carbon atom. For example, the term "neopentane" refers to a compound of the formula $C_5H_{12}$ and containing a quaternary carbon atom, otherwise known as 2,2-dimethylpropane.

Dimerization of Isobutylene

Often, diisobutylene is formed in the present invention via dimerization, preferably catalytic dimerization, of isobutylene. Preferably, the isobutylene is provided in a $C_4$ olefinic feed stream. Suitable $C_4$ olefinic feeds include $C_4$ hydrocarbon mixtures obtained in refining, cracking (thermal, catalytic cracking or steam cracking) and/or reforming of oils, butane-butene fractions obtained by removing butadiene from $C_4$ by-product fractions formed in the production of ethylene by thermal cracking of oils, or $C_4$ hydrocarbon mixtures obtained by dehydrogenation of hydrocarbon mixtures containing n-butane and isobutane. The $C_4$ olefinic feed stream preferably comprises a raffinate stream obtained from a refinery or chemical plant cracked naphtha stream, such as from a steam cracker or fluid catalytic cracker.

Often, the $C_4$ olefinic feed comprises: from about 5 wt % to about 60 wt % isobutylene, such as from about 10 wt % to about 50 wt % or about 20 wt % to about 40 wt %; from about 5 wt % to about 50 wt % 1-butene, such as from about 10 wt % to about 40 wt %; from about 5 wt % to about 50 wt % n-butane, such as from about 10 wt % to about 40 wt % or about 20 wt % to about 30 wt %; from about 5 wt % to about 50 wt % cis- and trans-2-butene, such as from about 10 wt % to about 40 wt % or about 20 wt % to about 30 wt %; and from about 1 wt % to about 20 wt % isobutane, such as from about 5 wt % to about 10 wt %, each by weight of the olefinic feed (100 wt %). The $C_4$ olefinic feed may also have minor amounts (0.01 wt % to 5 wt %) of polar molecules or molecules comprising polar moieties such as nitriles, mercaptans, or oxygenated components. Optionally, the $C_4$ olefinic feed may further comprise butadiene.

Preferably, the present process is highly selective for isobutylene homo-dimerization over co-dimerization of isobutylene with the other normal $C_4$ olefins of the feedstock. For example, preferably less than about 10 wt %, or preferably less than about 5 wt % of the n-butenes present in the feedstock are oligomerized.

Preferably, the dimerization is conducted in the presence of a catalyst. The catalyst employed in the dimerization reaction is generally acidic. Any catalyst suitable for olefin dimerization, whether homogeneous or heterogeneous, may be used, preferably heterogeneous. Examples of suitable acidic heterogeneous catalysts include zeolites, acidic metal oxides and mixed metal oxides, acidic ion exchange resins, acidic clays, aluminosilicates, solid phosphoric acid, and mixtures thereof. Non-limiting examples of such zeolites include those of the MFI framework type (e.g., ZSM-5), zeolite beta, mordenite, faujasite, and those of the MWW family (e.g., MCM-22, -49, or -56), especially those such zeolites having a high silicon to aluminum ratio (Si/Al), conveniently greater than 20:1, such as 50:1 or 100:1. Examples of metal oxides and mixed metal oxides are alumina, chloride- or fluorinated-alumina, silica-alumina, tungsten oxide on zirconia ($WO_x/ZrO_2$), molybdenum oxide on zirconia ($MoO_x/ZrO_2$), sulfated zirconia, or any other oxide that has acidic properties.

The dimerization reaction can be conducted in a wide range of reactor configurations including fixed bed (single or in series), slurry reactors, and/or catalytic distillation towers, preferably fixed bed. In addition, the dimerization reaction can be conducted in a single reaction zone or in a plurality of reaction zones. Generally, the dimerization reaction is conducted adiabatically, preferably within an adiabatic reaction vessel. Suitable reaction temperatures range from about 50° C. to about 350° C., such as from about 100° C. to about 300° C., or from about 150° C. to about 250° C. Preferably, the reaction pressure is maintained so that the $C_4$ olefinic feed remains in liquid form within the reactor. For instance, suitable reaction pressures are from about 100 kPa to about 7000 kPa absolute (e.g., atmospheric to about 1000 psia), such as from about 500 kPa to about 5000 kPa absolute.

Optionally, the $C_4$ olefinic feed may also be contacted with an oxygen-containing species, e.g., water or alcohol, prior to dimerization. In an embodiment, sufficient water or alcohol is used to saturate the $C_4$ olefinic feed. In particular, the $C_4$ olefinic feed may comprise from about 0.01 to about 0.25, alternatively, from about 0.02 to about 0.20, and alternatively, from about 0.03 to about 0.10, mol % water or alcohol based on the total hydrocarbon content of the $C_4$ olefinic feed. If desired, and by way of example, the water content of the $C_4$ olefinic feed may be increased by passage through a thermostatted water saturator.

Demethylation of Diisobutylene

The major components of the dimerization reaction effluent are generally to diisobutylene isomers (2,4,4-trimethyl-1-pentene, 2,4,4-trimethyl-2-pentene, or mixtures thereof), unreacted components of the $C_4$ olefinic feed, and some heavy $C_{12}+$ compound byproducts. The unreacted feed components and heavy byproducts can be readily removed from the reaction effluent by, for example, distillation.

The remainder of the dimerization reaction effluent, mainly composed of diisobutylene isomers, can be demethylated to produce neopentane. Preferably, the separated dimerization reaction effluent comprises greater than about 80 wt % diisobutylene, or greater than about 90 wt % diisobutylene, or greater than about 95 wt % diisobutylene, or greater than about 99 wt % diisobutylene, such as from about 90 wt % to about 100 wt % diisobutylene, or from about 95 wt %, to about 99 wt % diisobutylene.

Alternatively or additionally, an independent diisobutylene feed stream can be provided and demethylated. In such aspects, the diisobutylene feed stream preferably comprises greater than about 80 wt % diisobutylene, or greater than about 90 wt % diisobutylene, or greater than about 95 wt % diisobutylene, or greater than about 99 wt % diisobutylene, such as from about 80 wt % to about 99 wt % diisobutylene, or from about 85 wt % to about 95 wt % diisobutylene.

Whether the diisobutylene comprises the separated dimerization reaction effluent or is provided in an independent feed stream, the diisobutylene is mainly composed of two isomers: 2,4,4-trimethyl-1-pentene and 2,4,4-trimethyl-2-pentene. Where the diisobutylene comprises the separated dimerization reaction effluent, the ratio of 2,4,4-trimethyl-1-pentene and 2,4,4-trimethyl-2-pentene is dependent on the dimerization reaction conditions. In any embodiment, the ratio of 2,4,4-trimethyl-1-pentene and 2,4,4-trimethyl-2-pentene preferably ranges from 1:10 to 10:1.

Preferably, the demethylation is conducted via demethylation by contacting the diisobutylene isomers with hydrogen in the presence of a catalyst. The reaction pathway for the conversion of the two primary diisobutylene isomers to neopentane typically proceeds by hydrogenation to isooctane (2,2,4-trimethylpentane) followed by step-wise demethylation that may be summarized in the following reaction scheme:

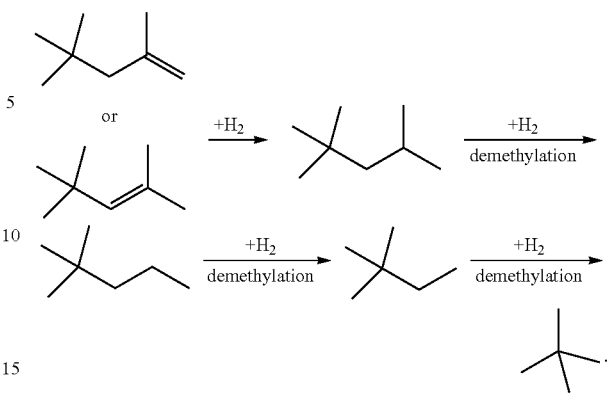

As shown from the reaction scheme above, the desired demethylation occurs at the tertiary (3°) carbon of the isooctane and the secondary (2°) carbon of the intermediates. Competing demethylation reactions can occur at the quaternary (4°) carbon. Advantageously, demethylation at the quaternary (4°) carbon in the present processes is minimized to prevent a loss of neopentane yield.

The demethylation reaction can be conducted in a wide range of reactor configurations including fixed bed (single or in series), slurry reactors, and/or catalytic distillation towers. In addition, the demethylation reaction can be conducted in a single reaction zone or in a plurality of reaction zones. The demethylation is conveniently conducted at a temperature from about 200° C. to about 500° C., such as from about 300° C. to about 400° C. and a pressure from about 100 kPa to about 10000 kPa absolute (e.g., atmospheric to about 1500 psia), such as from about 300 kPa to about 8000 kPa absolute, in the presence of a catalyst. Often, the demethylation is conducted at a hydrogen partial pressure of from about 50 kPa to about 3500 kPa absolute (e.g., from about 7 psia to about 500 psia). Preferably, the demethylation is conducted at a hydrogen partial pressure of less than about 2500 kPa, preferably less than about 2200 kPa, and preferably less than about 1000 kPa (e.g., preferably less than about 350 psia, or preferably less than about 150 psia).

Generally, the catalyst employed in the demethylation comprises a transition metal component. Specific, non-limiting examples of suitable transition metal components include Fe, Co, Ni, Rh, Ir, Ru, Pt, and Pd, combinations thereof, compounds thereof, and mixtures of compounds thereof, with Ni being particularly advantageous. Often, the transition metal component contains transition metal as a single component. Alternatively, the transition metal component may contain a transition metal combined with an additional metal to form a binary or ternary alloy. Specific, non-limiting examples of suitable additional metals include Cu, Au, Ag, Sn, Zn, Re, combinations thereof, compounds thereof, and mixtures of compounds thereof. Desirably, the amount of the transition metal component present in the catalyst is from about 0.05 wt % to about 60.0 wt %, such as from about 0.10 wt % to about 50.0 wt %, of the total weight of the catalyst. Generally, the transition metal component is supported on a non-acidic support material. Specific, non-limiting examples of suitable support materials include silica, theta-alumina, clay, pentasil, aluminophosphate, carbon, titania, zirconia, and mixtures thereof.

Preferably, the acidity of the catalyst employed in the demethylation is minimized to inhibit undesired cracking reactions. Often, the acidity of the catalyst is reduced via impregnation with an alkali metal compound, preferably an alkali metal hydroxide, nitrate, carbonate, bicarbonate, or oxide, such as sodium oxide, e.g., $Na_2O$. Desirably, the amount of the alkali metal compound present in the catalyst is from about 0.05 wt % to about 1.0 wt %, such as from about 0.1 wt % to about 0.5 wt %, of the total weight of the catalyst.

Typically, the diisobutylene conversion during the demethylation step is greater than 80%, preferably greater than 90%, preferably greater than 95%, and preferably greater than 99%, such as from 80% to 99% or 90% to 99%. The product of the demethylation step generally comprises neopentane, $C_4$- hydrocarbon components (e.g., methane, ethane, and propane) and, optionally, partially converted $C_6$+ hydrocarbon intermediate components (e.g., neohexane and neoheptane). Preferably, the product of the demethylation step comprises: at least about 10 wt %, preferably at least about 25 wt %, preferably at least about 35 wt %, and ideally at least about 50 wt % of neopentane, such as from about 25 wt % to about 50 wt % or from about 30 wt % to about 40 wt %; less than about 75 wt %, preferably less than about 65 wt %, and preferably less than about 50 wt % of $C_4$- hydrocarbon components, such as from about 25 wt % to about 75 wt % or from about 40 wt % to about 60 wt %; less than about 5 wt %, preferably less than about 1 wt %, and ideally less than about 0.5 wt % of non-neopentane $C_5$ hydrocarbon components, such as from about 0 wt % to about 1 wt %; and less than about 10 wt %, preferably less than about 5 wt %, preferably less than about 1 wt %, and ideally less than about 0.5 wt % of partially converted $C_6$+ hydrocarbon components (e.g., $C_6$-$C_8$ hydrocarbons), such as from about 0 wt % to about 10 wt %, or from about 0 to about 1 wt %, or from about 0.5 wt % to about 1 wt %.

The light $C_4$- hydrocarbon components and the $C_6$+ hydrocarbon intermediate components can be readily removed from the demethylation product by, for example, distillation, thereby yielding a purified neopentane product stream. Preferably, the purified neopentane product stream comprises greater than about 80 wt % neopentane, or greater than about 90 wt % neopentane, or greater than about 95 wt % neopentane, or greater than about 99 wt % neopentane, such as from about 80 wt % to about 99 wt % neopentane, or from about 85 wt % to about 95 wt % neopentane.

Process

The present inventive process will now be more particularly described with reference to the FIGURE. The FIGURE illustrates one aspect of the present inventive process, in which a $C_4$ olefinic feed stream comprising isobutylene is fed to a dimerization reactor to produce a dimerization product, after which diisobutylene is separated and demethylated. A resulting $C_6$+ hydrocarbon stream is optionally recycled to the demethylation step. The invention is not limited to this aspect, and this description is not meant to foreclose other aspects within the broader scope of the invention, such as those where an independent diisobutylene feed stream is provided and demethylated.

As shown in the FIGURE, a $C_4$ olefinic feed stream 101 comprising isobutylene is fed to a dimerization reactor 102 to produce a dimerization effluent 103 comprising diisobutylene, unreacted $C_4$ hydrocarbons, and byproducts, e.g., $C_{12}$+ hydrocarbons. The dimerization effluent is then fed to a separator 104, e.g., a distillation column, to separate a light fraction 105 comprising unreacted $C_4$ hydrocarbons and a heavy fraction 106 comprising $C_{12}$+ hydrocarbons from the dimerization effluent. The resulting obtained fraction 107 is mainly composed of diisobutylene isomers. The light fraction 105 can be subjected to further downstream processing, such as recovery of n-butenes (not shown). Preferably, the heavy fraction 106 may be used for fuel (not shown). Fraction 107 and a hydrogen feed stream 109 are then introduced to a demethylation reactor 108 to produce a demethylation effluent 110 comprising neopentane, light byproducts, e.g., $C_4$- hydrocarbons, partially converted components, e.g., $C_6$-$C_8$ hydrocarbons, and, optionally, unreacted diisobutylene. The demethylation effluent 110 is then fed to a separator 111, e.g., a distillation column, to separate a light fraction 112 comprising $C_4$- hydrocarbons and a heavy fraction 113 comprising partially converted $C_6$+ hydrocarbons (primarily, $C_6$-$C_8$ hydrocarbons) and, optionally, unreacted diisobutylene from the demethylation effluent 110. The resulting obtained fraction 114 is mainly composed of neopentane. The light fraction 112 can be subjected to further downstream treatment for use as fuel (not shown). Optionally, the heavy fraction 113 can be recycled to the demethylation reactor.

Neopentane produced in accordance with the present invention is useful as a blowing agent for the production of foamed polymers and possesses several properties (e.g., a boiling point of 9.5° C. and a freezing point of −16.6° C.) making it useful as a heat removal agent and/or as an inert condensing agent (ICA) in gas phase polymerization process, such as gas phase polymerization processes for the production of polyethylene. Neopentane produced in accordance with this invention also exhibits high octane numbers and is therefore useful as a gasoline blend component.

The invention will now be more particularly described with reference to the following non-limiting Examples.

EXAMPLES

Demethylation of Diisobutylene

A diisobutylene feed was demethylated in the presence of a Ni/Kieselguhr catalyst (60 wt % Ni on Kieselguhr clay, Sigma-Aldrich) (0.528 g) using a down-flow, tubular, fixed bed reactor and process described below.

Catalytic reactions were performed using a down-flow, tubular, fixed-bed reactor equipped with two 100-mL ISCO pumps and various gas feeds. The liquid feed was delivered via the ISCO pumps, mixed with gas feed through a heated section for vaporization before entering the reactor (⅜ in O.D.×16¾ in×0.028 in wall stainless steel tube) (1 cm×43 cm×0.07 cm). Catalyst (0.25-2 g loading) was pelletized and sized to 20-40 mesh, diluted with quartz chips to a total volume of 5 mL and loaded in the isothermal zone of the reactor. A piece of ¼ in (0.6 cm) O.D. stainless steel tubing was inserted at the bottom of the reactor tube to ensure the catalyst bed being located in the isothermal zone of the furnace. Glass wool was used at the top and bottom of the catalyst bed to keep the catalyst bed in place. Reactor pressure was controlled via a research control valve (RCV) at the exit of the reactor and the reactor effluent was heat-traced and sent to a gas chromatograph (GC) for on-line analysis.

The catalyst was first purged with $N_2$ and then heated to 300° C.–500° C. at a ramp rate of 3° C./min under flowing $H_2$ (100 cc/min) and held 2-4 h for reduction. After reduction, the reactor was cooled down to the operating temperature. The liquid feed was then introduced and $H_2$ flow rate adjusted accordingly at the desired operating pressure.

An Agilent HP7890™ GC having a Restek 30 m×0.32 mm×5 μm GC column (Rtx™-1, Catalog #10178) was used for product analysis. The injector was set at 260° C. and the detector at 280° C. The column flow rate was 1.2 cc/min He, with typical air and $H_2$ flows for the detector. The oven temperature was programmed in the following manner: initial temperature of 40° C.; hold for 5 min; ramp at 4° C./min to 200° C.; ramp at 20° C./min to 260° C. for bake out. The total reactor effluent was sampled and analyzed hourly. GC peaks were identified using the "Alphagaz PIANO Calibration Standards" (Supelco Product #4-4586-U, available from Sigma-Aldrich) and authentic samples, using a response factor of one for all components.

The theoretical neopentane yield using this described process was estimated to be ca. 60 wt %. The results of the GC testing of the reactor effluent at various reaction conditions are summarized in Table 1.

TABLE 1

[1.01 g catalyst, reduced at 500° C. (4 h, 100 cc/min $H_2$); Feed Liquid Weight Hourly Space Velocity (LWHSV) = 4 $h^{-1}$; $H_2$ Flow Rate = 36 cc/min; $N_2$ Flow Rate = 61 cc/min]. TM1P = 2,4,4-trimethyl-1-pentene; TM2P = 2,4,4-trimethyl-2-pentene

| Temp (° C.) | 250 | 275 | 285 | 285 | 285 |
|---|---|---|---|---|---|
| Pressure (psia) | 115 | 115 | 115 | 45 | 315 |
| p $H_2$ (psia) | 41 | 41 | 41 | 16 | 113 |
| TM1P conv. (%) | 99.9 | 99.5 | 99.9 | 100 | 99.9 |
| TM2P conv. (%) | 100 | 100 | 100 | 100 | 100 |
| Sel. (wt %) | | | | | |
| Methane | 2.9 | 27.1 | 40.1 | 50.7 | 1.1 |
| Ethane | | 0.6 | 2.2 | 4.7 | |
| Propane | | 1.0 | 3.9 | 4.9 | |
| 2-Methylpropane | 0.1 | 2.5 | 4.4 | 3.5 | 0.3 |
| n-Butane | | 1.0 | 1.4 | 0.4 | |
| 2,2-Dimethylpropane | 0.2 | 10.1 | 24.4 | 25.1 | |
| 2-Methylbutane | 0.1 | 1.9 | 0.8 | 0.1 | |
| n-Pentane | | 0.7 | 0.2 | | |
| 2,2-Dimethylbutane | 2.1 | 33.1 | 21.1 | 10.4 | 0.7 |
| 2-Methylpentane | | 1.0 | | | |
| 3-Methylpentane | 0.1 | 0.1 | | | |
| 2,2-Dimethylpentane | 9.3 | 16.2 | 1.2 | 0.2 | 4.5 |
| 2,4-Dimethylpentane | 0.6 | 0.1 | | | 0.2 |
| 2,2,3-Trimethylbutane | 0.1 | 0.4 | | | |
| 3,3-Dimethylpentane | | 0.8 | 0.1 | | |
| 2,3-Dimethylpentane | 0.3 | | | | 0.2 |
| 3-Methylhexane | 0.2 | 0.2 | | | |
| 2,2,4-Trimethylpentane | 81.4 | 3.0 | | | 90.4 |
| 2,2-Dimethylhexane | 1.0 | 0.2 | | | 1.1 |
| 1,1,3-Trimethylcyclopentane | 0.5 | | | | 0.2 |
| 2,2,3-Trimethylpentane | 0.7 | | | | 0.9 |
| 2,3-Dimethylhexane | 0.2 | | | | 0.3 |

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of," "consisting of," "selected from the group consisting of," or "is" preceding the recitation of the composition, element, or elements and vice versa.

What is claimed is:

1. A process for producing neopentane, the process comprising:
   (a) providing a feed stream including isobutylene;
   (b) dimerizing the isobutylene to produce a dimerization product including diisobutylene; and
   (c) demethylating the diisobutylene in a continuous flow, fixed bed reactor at a temperature range of from 250 to 350° C., a hydrogen partial pressure of from about 7 psia to about 113 psia, and in the presence of a catalyst comprising a support material comprising Ni and compounds thereof to produce a demethylation product including at least 10 wt % neopentane based on the weight of the demethylation product; wherein the catalyst further comprises at least one member selected from the group consisting of Cu, Au, Ag, Sn, Zn, Re, combinations thereof, compounds thereof, and mixtures of compounds thereof.

2. The process of claim 1, wherein at least part of the diisobutylene is separated from the dimerization product prior to demethylation.

3. The process of claim 2, wherein separating the diisobutylene from the dimerization product comprises distillation.

4. The process of claim 3, wherein the dimerization product is separated into fractions comprising (1) a $C_4$ hydrocarbon fraction (2) a diisobutylene fraction and (3) a $C_{12}+$ hydrocarbon fraction.

5. The process of claim 1, wherein the feed stream comprises a raffinate stream obtained from cracking a naphtha stream.

6. The process of claim 5, wherein the feed stream comprises from about 5 wt % to about 60 wt % isobutylene based on the weight of the feed stream.

7. The process of claim 1, wherein the catalyst (A) comprises at least one member selected from the group consisting of acidic ion-exchange resin, acidic clay, aluminosilicate, supported phosphoric acid, acidic metal oxide, acidic mixed metal oxide, zeolites, and mixtures thereof.

8. The process of claim 1, wherein the dimerization is carried out within an adiabatic reaction vessel.

9. The process of claim 1, further comprising contacting the feed stream with an oxygen-containing species prior to the dimerization.

10. The process of claim 1, wherein the demethylation product comprises from about 25 wt % to about 50 wt % neopentane based on the weight of the demethylation product and from about 0 wt % to about 10 wt % $C_6+$ hydrocarbon components based on the weight of the demethylation product.

11. A process for producing neopentane, the process comprising:
    (a) providing a stream including diisobutylene; and
    (b) demethylating the diisobutylene in a continuous flow, fixed bed reactor at a temperature range of from 250 to 350° C., a hydrogen partial pressure of from about 7 psia to about 113 psia, and in the presence of a catalyst comprising a support material comprising Ni and compounds thereof to produce a demethylation product including at least 10 wt % neopentane based on the weight of the demethylation product; wherein the catalyst further comprises at least one member selected from the group consisting of Cu, Au, Ag, Sn, Zn, Re, combinations thereof, compounds thereof, and mixtures of compounds thereof.

12. The process of claim 1, further comprising separating at least part of the neopentane from the demethylation product.

13. The process of claim 12, wherein separating the neopentane from the demethylation product comprises distillation.

14. The process of claim 13, wherein the demethylation product is separated into fractions comprising (1) a $C_4$-hydrocarbon fraction, (2) a neopentane fraction, and (3) a $C_6+$ hydrocarbon fraction.

15. The process of claim 14, wherein the demethylation is carried out in a reaction vessel, and wherein the $C_6+$ hydrocarbon fraction is recycled to the reaction vessel.

16. The process of claim 11, wherein the catalyst comprises a support material selected from the group consisting of silica, theta-alumina, clay, pentasil, aluminophosphate, carbon, titania, zirconia, and mixtures thereof.

* * * * *